United States Patent [19]
Butts

[11] Patent Number: 5,418,131
[45] Date of Patent: May 23, 1995

[54] HUMIDITY COMPENSATED CARBON DIOXIDE GAS MEASUREMENT AND CONTROL

[75] Inventor: Charles G. Butts, Weaverville, N.C.

[73] Assignee: General Signal Corporation, Stamford, Conn.

[21] Appl. No.: 226,964

[22] Filed: Apr. 13, 1994

[51] Int. Cl.[6] .................. A01K 31/20; C12M 1/36; C12Q 3/00
[52] U.S. Cl. .......................... 435/3; 435/284; 435/289; 435/291; 435/809; 422/98; 422/104; 422/108; 422/110; 422/123; 436/133; 236/2; 236/3; 237/14
[58] Field of Search ............... 422/62, 98, 99, 108, 422/104, 110, 111, 119, 123; 436/133; 435/3, 284, 289, 291, 809; 236/2, 3; 237/14; 62/78; 165/30

Primary Examiner—David A. Redding
Attorney, Agent, or Firm—Ohlandt, Greeley, Ruggiero & Perle

[57] ABSTRACT

A carbon dioxide gas measurement and control system which comprises a thermal conductivity $CO_2$ sensor and a humidity sensor which produce separate and independent output signals which are compared in a microprocessor, thereby generating a humidity compensated carbon dioxide gas measurement which is accurate to within ±0.1%.

24 Claims, 4 Drawing Sheets

HUMIDITY COMPENSATED CARBON DIOXIDE GAS MEASUREMENT AND CONTROL

The present invention relates generally to a method and system for accurately measuring carbon dioxide gas concentration in a substantially saturated or non-saturated gaseous environment, e.g., a cell-culture incubator, regardless of absolute humidity changes.

BACKGROUND OF THE INVENTION

Measurement and control of the $CO_2$ concentration in laboratory cell-culture incubators is most commonly accomplished by means of a thermal conductivity detection system. The thermal conductivity cell, or detector, is a differential thermometer, set up as an electronic bridge circuit that is balanced to be equal, with two thermistors in a common block or metallic housing to add thermal stability. (See U.S. Pat. No. 3,929,584, ((Mansfield)). This cell is most commonly placed in a working environment that is isolated from the surrounding area, but is not restricted to its placement. In some instances, the detector cell is located in an air flow path external from the working environment, but contiguous with the environment. One thermistor sensor is enclosed in the block/housing and detects chamber temperature only. The other thermistor sensor is exposed to the chamber environment. The measured difference between the two thermistor sensors is the thermal conductivity (density) of the atmosphere, or its ability, when moved at an even rate, to remove the small amount of heat from the exposed sensor. If all other factors remain constant and only the carbon dioxide content is varied, the "TC" cell output (when properly calibrated) will indicate changes in $CO_2$ concentration. Unfortunately, the TC cell is affected by barometric pressure, temperature, humidity and the velocity of air flow past the sensor cell. These variables are controlled or compensated for with the use of electronic zeroing circuitry to compensate for changes in temperature and relative humidity levels. In monitoring the effects of $CO_2$ in an atmosphere, absolute humidity must be held constant so any change in thermal conductivity is caused only by a change in the $CO_2$ concentration. Under the worst circumstances, a change in absolute humidity can cause such a significant change in thermal conductivity that the controller can shift the $CO_2$ content by as much as 4%.

To maintain a stable humidity level in laboratory incubators, a pan of water is placed within the working environment and its temperature allowed to equilibrate. The incubator, working atmosphere, must reach a point of near saturation in order to maintain an absolute humidity level that will not change with ambient conditions.

For the laboratory investigator that does not want to operate their incubator in a saturated condition, but does want accurate $CO_2$ control, the drifting of the thermal conductivity sensor's reference becomes a problem with regard to the accuracy of the $CO_2$ gas concentration in the incubator. That is, as the absolute humidity changes, so does the reference base of the $CO_2$ gas sensor.

When operating a dry incubator, as opposed to a saturated one, ambient humidity fluctuations will effect $CO_2$ zero calibration. Since the fluctuations possible in extreme ambient temperature changes have less effect on the total absolute humidity, the $CO_2$ calibration can be affected as much as 1½% in the worst case which does not represent as severe a problem, but does create an error that could prove critical in the pH level of the cell media being cultured within the incubator working chamber.

The present inventor has developed a unique system for detecting or measuring $CO_2$ gas concentration in an enclosed environment using a thermal conductivity sensor without the inaccuracies of the prior art systems which are caused by fluctuations in absolute humidity. The present invention removes the inaccuracies due to the effect of changes in absolute humidity levels on the zero calibration point of the thermal conductivity sensor which is used to measure and control the $CO_2$ content within any controlled atmosphere (e.g., a cell-culture $CO_2$ incubator). This is accomplished by having the output of the thermal conductivity detector multiplexed with the output of an absolute humidity detector via firmware in a microprocessor control system. The output from the microprocessor controller is a humidity-corrected signal that will maintain a stable reference output with respect to constantly changing absolute humidity levels in the controlled atmosphere. By constantly correcting this output due to changes in absolute humidity levels, accuracy and errors were reduced from a high of 4% for conventional systems to less than 0.2% for the present invention. These errors are primarily caused by manually or automatically zeroing the thermal conductivity detection system in a potentially unstable environment. This zeroing is typically conducted by the product user or non-compensating type control system.

The present invention is also capable of specifically measuring and controlling the $CO_2$ content in an enclosed (e.g., a laboratory $CO_2$ incubator) by means of a thermal conductivity detector, where the relative humidity level may be allowed to equilibrate to that of surrounding ambient conditions as well as conditions that may be increased to virtual saturation.

The two factors that contribute to inaccuracies in a thermal conductivity gas control system, i.e., relative humidity and dry-bulb temperature, are taken into consideration in the measurement system of the present invention to arrive at the absolute humidity compensated carbon dioxide gas concentration.

The present invention also provides many additional advantages which shall become apparent as described below.

SUMMARY OF THE INVENTION

A humidity compensated carbon dioxide gas measurement and control system for use in a substantially saturated or non-saturated gaseous environment which comprises: a humidity sensor means capable of providing a humidity level output; a thermal conductivity sensor means capable of providing a carbon dioxide concentration output; means for comparing the humidity level output with a stored humidity level output to establish a compensation value or factor, the stored humidity level is the stored humidity level output at the initial zero reference of the carbon dioxide gas; and means for adjusting the carbon dioxide concentration output in accordance with the compensation value or factor, thereby generating a humidity compensated carbon dioxide gas concentration output. The system may also include a means for controlling the flow of carbon dioxide gas into the environment in accordance with the humidity compensated carbon dioxide gas concentration output. It is also desirable to have a means for measuring the temperature of the environment in order to adjust the humidity level output accordingly.

The present invention also includes a process for measuring and controlling carbon dioxide gas in a substantially saturated or non-saturated environment which comprises: measuring the humidity level of the environment; measuring the carbon dioxide concentration of the environment; comparing the humidity level with a stored humidity level to establish a compensation value or factor, the stored humidity level is the stored humidity level output at the initial zero reference of the carbon dioxide gas; and adjusting the carbon dioxide concentration in accordance with the compensation value or factor, thereby generating a humidity compensated carbon dioxide gas concentration measurement. Preferably, the flow of the carbon dioxide gas into the environment can be regulated in accordance with the humidity compensated carbon dioxide gas concentration measurement.

Other and further objects, advantages and features of the present invention will be understood by reference to the following specification in conjunction with the annexed drawings, wherein like parts have been given like numbers.

DESCRIPTION OF THE PREFERRED EMBODIMENTS

A thermal conductivity $CO_2$ sensor measurement output signal is multiplexed with an absolute humidity sensor measurement output signal via a microprocessor. The sensors are disposed within an enclosed container (i.e., a cell culture incubator) such that they are within the path of the circulating $CO_2$ gas. Both the $CO_2$ and absolute humidity detection devices are connected, via a shielded interconnecting cable, to their respective electronic interface circuit board. The electronically conditioned signals generated from both the $CO_2$ and absolute humidity sensors are then independently passed on to a microprocessor for firmware multiplexing. As changes are detected by the absolute humidity sensor, adjustments are electronically made on a continuous basis to the zero reference base of the thermal conductivity gas control circuit. This compensation system maintains an accurate gas control system that is unaffected by changes in absolute humidity levels.

Figure 1:
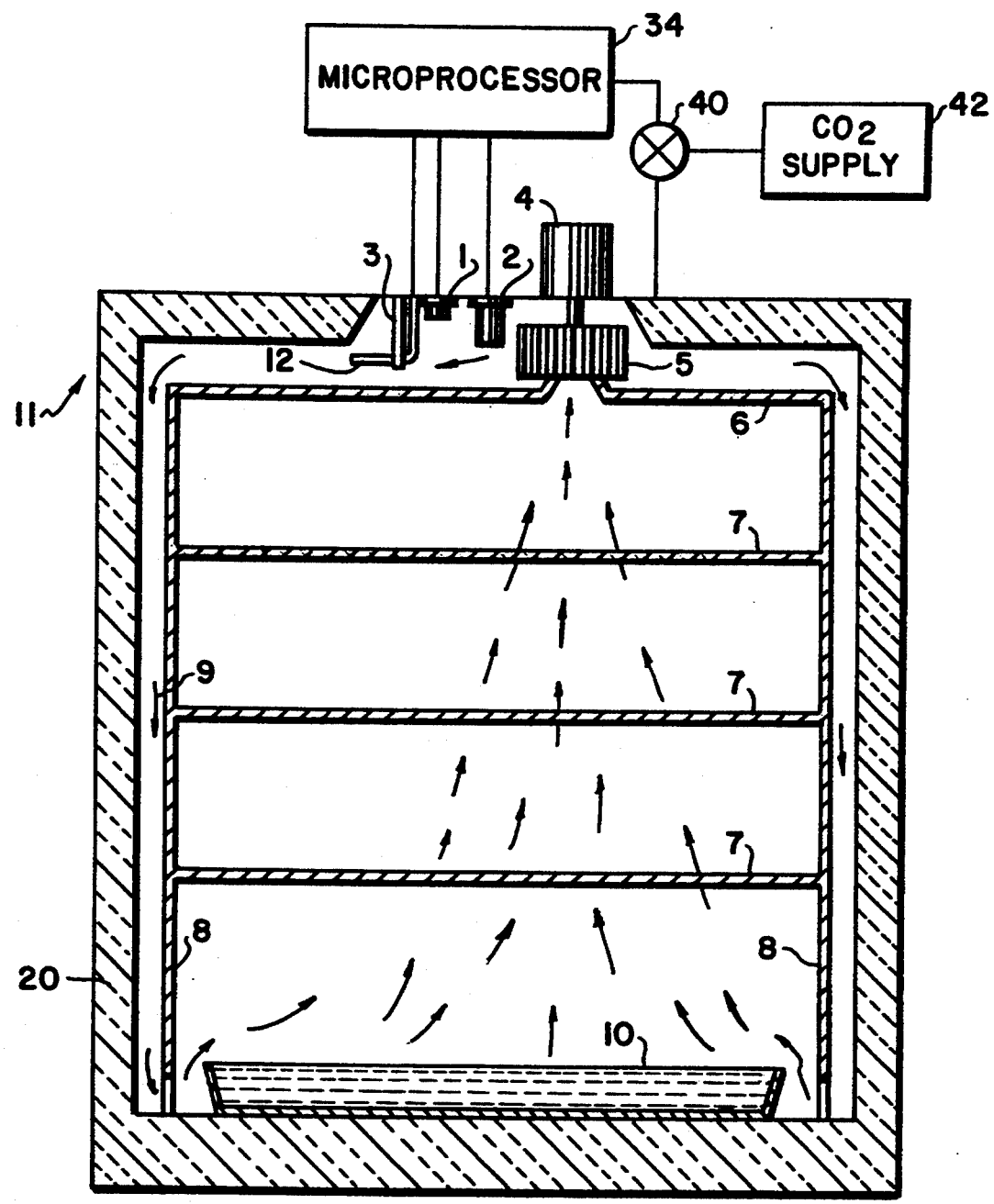
FIG. 1 is a schematic representation of an incubator having humidity, $CO_2$ and temperature sensors disposed therein according to the present invention.

FIG. 1 shows a cell-culture incubator 11 comprising multiple perforated shelves 7 disposed between wall ducts 8. The outer surface of wall ducts 8 and the inner surface of incubator housing 20 form a passageway 9 therebetween, wherein gas contained within housing 11 is circulated in the direction of the arrows such that gas moves from the humidity water pan 10 up towards blower wheel 4 attached to blower motor 4 and returned to the bottom of incubator 11 via passageways 9. As the gas is dispelled from blower wheel 5 it passes over humidity sensor 1, thermal conductivity sensor 2 and temperature sensor 3.

Figure 2:
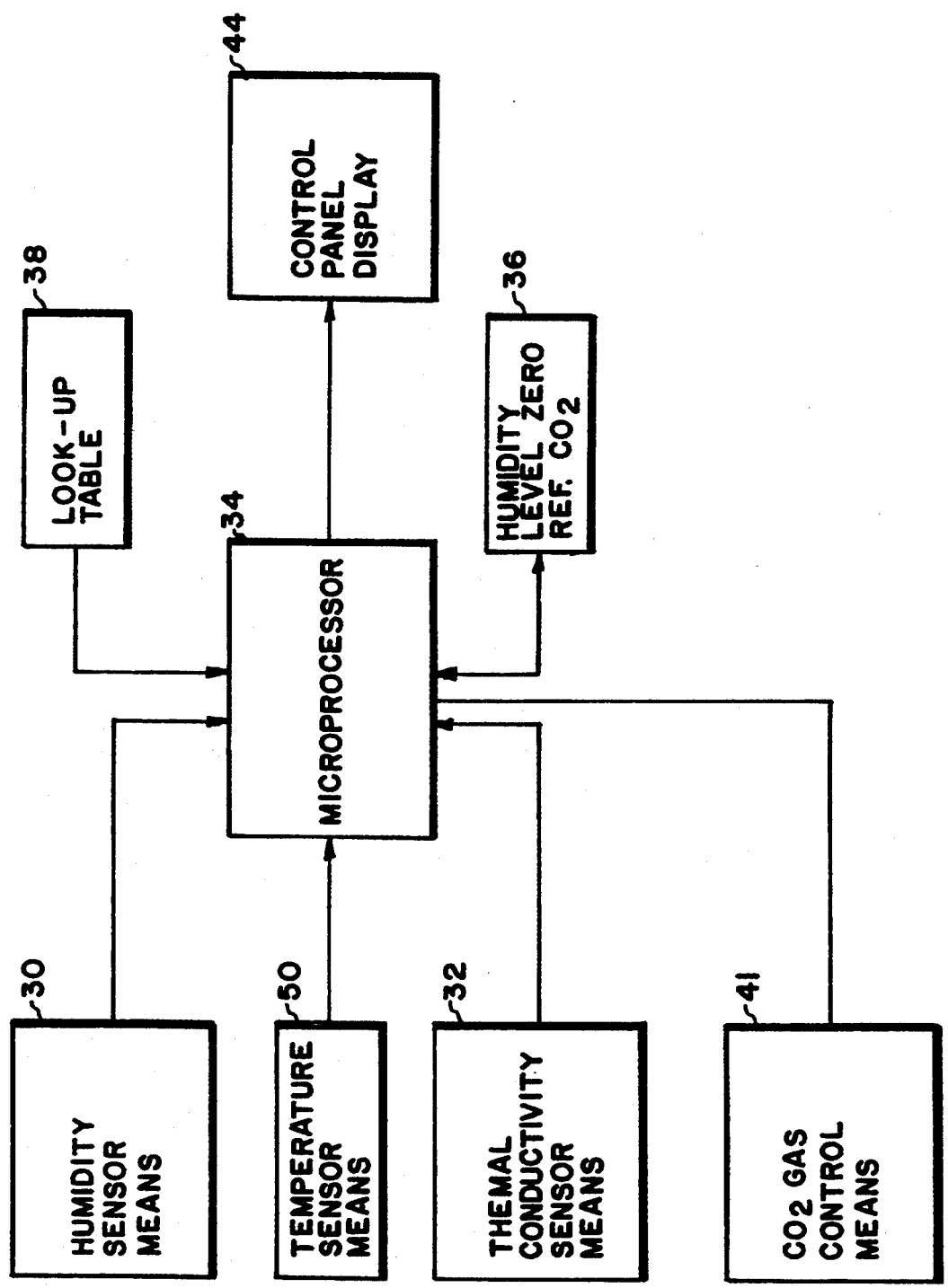
FIG. 2 is a block diagram of the humidity compensated $CO_2$ gas measurement and control system in accordance with the present invention.

The humidity level and $CO_2$ sensors interact with a microprocessor in accordance with the block diagram shown in FIG. 2. The humidity sensor means 30 is capable of accurately measuring the environmental atmosphere to detect the presence of humidity that is temperature compensated for stability and accuracy over the entire operating range of the system. As such incubator 11 having a heat generating means will form an environmentally controlled chamber useful for research of cell studies in the laboratory requiring specific control of surrounding temperature and pH levels. Pressurized carbon dioxide is externally supplied and connected to incubator 11 and its flow controlled by means of a solenoid valve 40 disposed between $CO_2$ supply means 42 and incubator 11.

The level of carbon dioxide in the controlled atmosphere chamber 13 of incubator 11 is typically maintained at a constant level, impervious to changes in temperature and humidity levels, by microprocessor 34 which continuously monitors these parameters and maintains the desired $CO_2$ concentration level by proportionally opening and closing solenoid valve 40 allowing pressurized $CO_2$ supplied via storage tank 42 to enter controlled atmosphere chamber 13.

The thermal conductivity cell, or detector, 2 is a differential thermometer, set up as an electronic bridge circuit that is balanced to be equal, with two thermistors in a common block or metallic housing to add thermal stability. That is, the thermal conductivity of the $CO_2$ disposed within chamber 13 is continuously measured by a thermistor that is part of a Wheatstone bridge circuit that also provides a linear voltage output for use by microprocessor 34.

The humidity system's sensor 2 utilizes a monolithic integrated circuit detector 30 coupled with a thin film platinum RTD sensor 50 for temperature measurement and compensation within the humidity detection system for stability over the entire incubator operating humidity range. The monolithic integrated circuit used for humidity measurement is a capacitance sensor, when incorporated in a complimentary metal oxide semiconductor (CMOS) circuit, such that it converts the signal into a linear voltage output for use by microprocessor control system 34.

Figure 4:
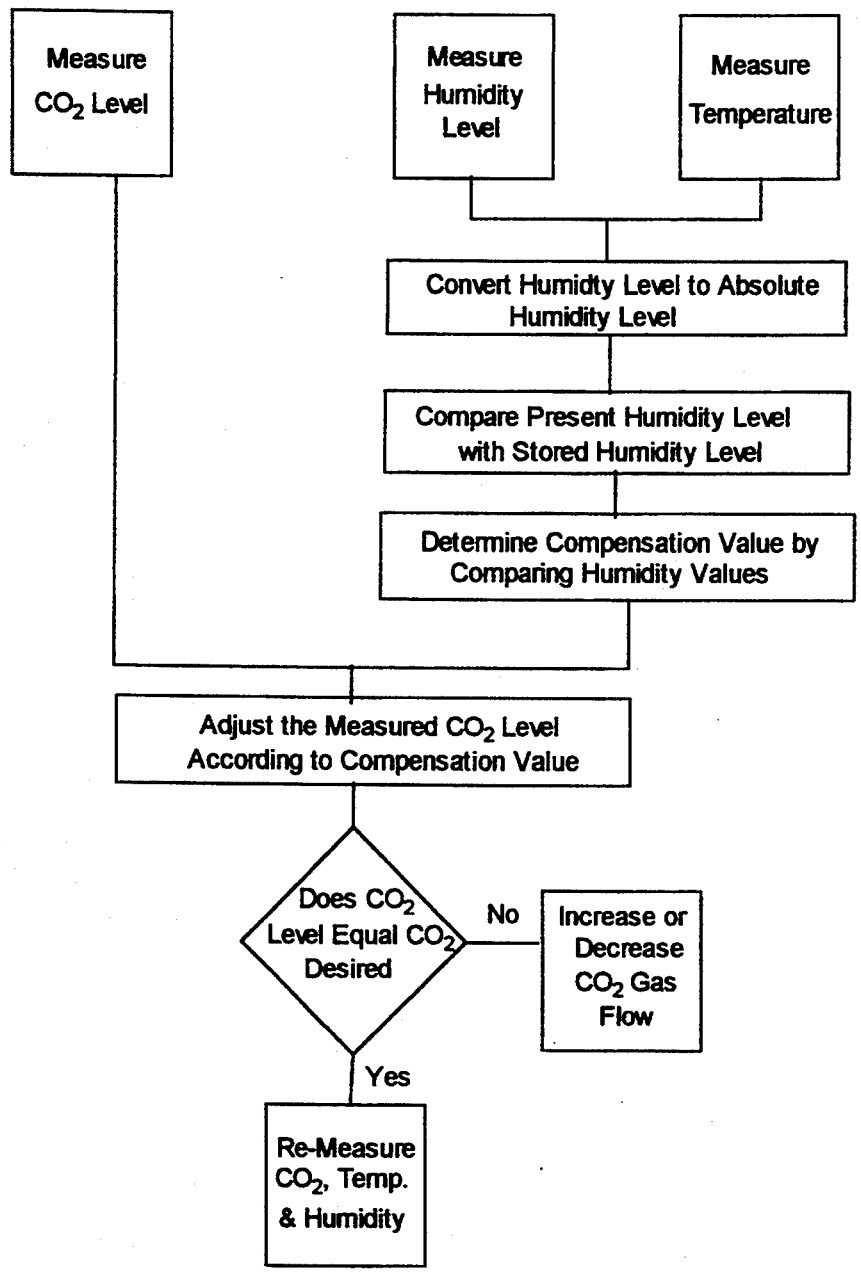
FIG. 4 is a flow chart of the process steps used to compensate $CO_2$ gas measurements for changes in absolute humidity.

These two signals are multiplexed together within microprocessor 34 using firmware. Microprocessor 34 then compares the present humidity level detected by humidity sensor means 30 with the stored humidity level 36 detected when the zero reference of the $CO_2$ was originally set or calibrated. A compensation value is then established, similar to an offset, by comparing values in look-up table 38. Look-up table 38 comprises differential data that represents specific values to offset the $CO_2$ gas control system zero reference point. The difference between the two humidity measurements is then referenced to the actual value of the $CO_2$ measured by thermal conductivity sensor means 32. The measured $CO_2$ concentration is then adjusted according to this differential and the output is passed to control panel display 44 for user reference. Once the actual $CO_2$ concentration is detected and re-calibrated, microprocessor 34 signals $CO_2$ gas control means 41 to either open or close solenoid valve 40 to allow pressurized $CO_2$ to enter chamber 13 in order to maintain a desired $CO_2$ concentration level therein. FIG. 4 is a flow chart of the process steps discussed immediately above.

Figure 3:
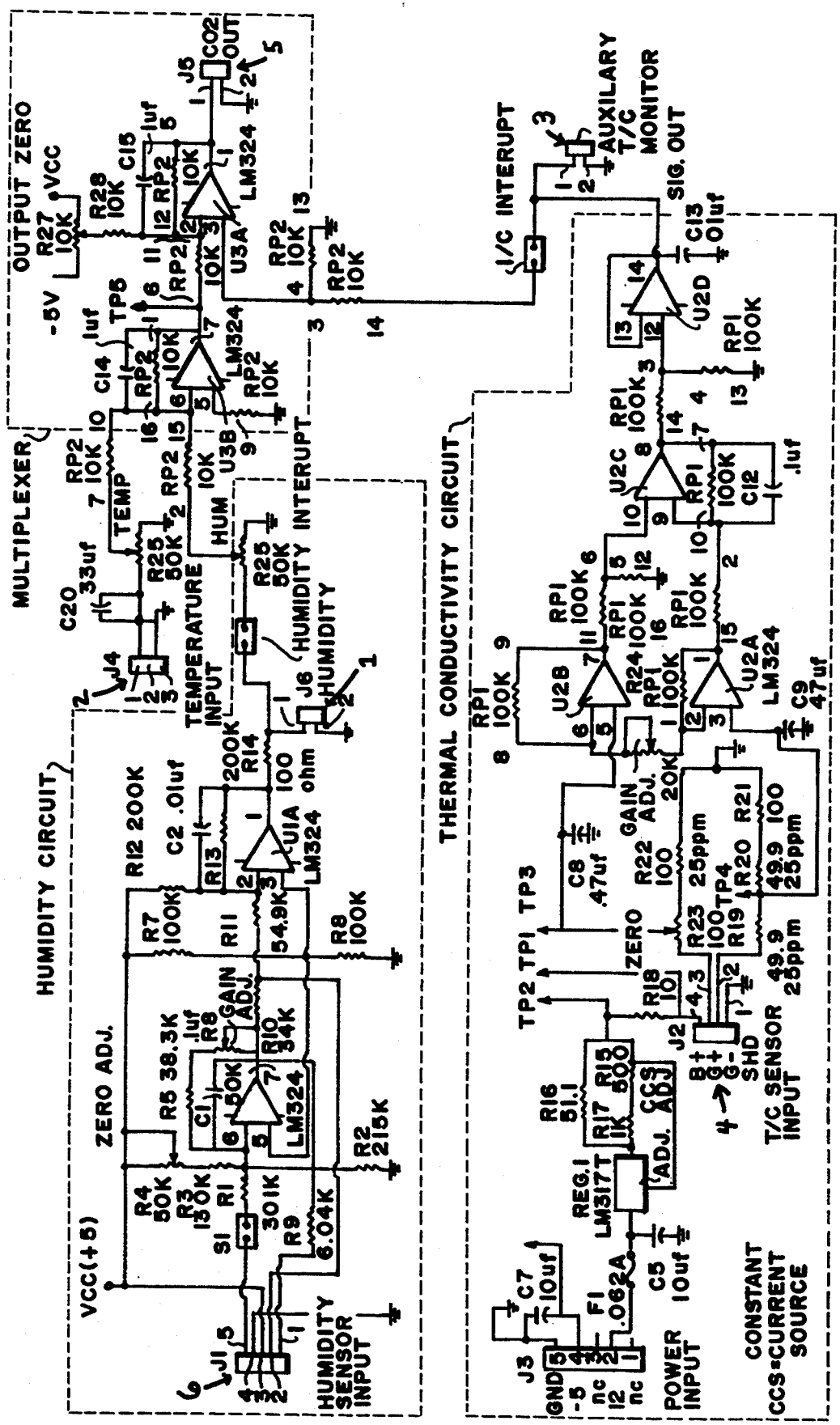
FIG. 3 is a circuitry diagram of the humidity compensated $CO_2$ gas measurement and control system in accordance with the present invention.

FIG. 3 shows the circuitry used in accordance with the present invention, wherein the humidity level is input into the electronic circuit system from the combination humidity/temperature sensor, not shown, located within the working environment. The humidity/temperature sensor is connected to the electronic circuit system via humidity sensor input 6. The humidity level input is conditioned by operational amplifier U1A whose output then goes directly to the humidity circuitry on the microprocessor circuit board via output 1 which is then passed on to the humidity parameter display of the incubator. Simultaneously, the conditioned output from operational amplifier U1A is passed on to the multiplexing circuitry.

The humidity/temperature sensor is also connected to the electronic circuit system via temperature sensor input 2. The temperature level input is combined with the conditioned humidity level input via operational amplifier U3B, wherein a correction factor is applied to the combined signals which is then converted to an absolute humidity value.

The carbon dioxide sensor is connected to the electronic circuit system via carbon dioxide sensor input 4. The signal received from input 4 is conditioned by operational amplifier U2A. This conditioned output signal goes directly to the auxiliary thermal-conductivity monitoring circuitry on the microprocessor circuit board via output 3. Simultaneously, the conditioned output signal is also passed on to the multiplexing circuitry. That is, the conditioned carbon dioxide output signal from U2D is sent to the multiplexing circuitry where it is multiplexed with the zero corrected, absolute humidity output from U3B (i.e., U3B adds correction for varying absolute humidity levels from zero referenced Rh level) and then goes directly to the monitoring circuitry on the microprocessor circuit board via output 5.

The carbon dioxide and humidity levels are compared, the absolute humidity output is verified with the absolute humidity level detected when the carbon dioxide gas system zero was referenced, and the carbon dioxide gas system internal zero reference is adjusted (i.e., compensated) if there has been any absolute humidity level changes. Any carbon dioxide set point error is corrected by the addition of carbon dioxide gas. This is performed by providing a voltage output that opens a solenoid valve that allows carbon dioxide to enter the working environment in metered amounts.

This type of control and compensation system is accurate to within ±0.1% of the actual concentration measured. The total error created by temperature and humidity changes can subsequently be held to approximately ±0.1% as well as relating to the resolution capability of the output display.

EXAMPLE 1

For example, an incubator operating at 37° C. with an ambient relative humidity level of 35% (absolute humidity is equal to 102 grains of moisture per pound of dry air), and with the $CO_2$ detector system zero calibrated under these conditions, maintains the $CO_2$ gas level at 5% of the environment. Water is now placed in the incubator to raise its humidity level to saturation. After stabilization, the temperature remains at 37° C. and the $CO_2$ concentration is based on the displayed value. The relative humidity in the incubator should now be approximately 98% (absolute humidity is equal to 308 grains of moisture per pound of dry air). A verification of the actual $CO_2$ concentration reveals that it is now approximately 9% of the environment.

This example shows what can happen if an incubator is $CO_2$ zero calibrated dry and, thereafter, water is added without re-zeroing. That is, if an incubator is zeroed the actual $CO_2$ content differs by almost 4% from that shown on the display.

EXAMPLE 2

An incubator utilizing a humidity compensated $CO_2$ gas measurement and control system according to the present invention was heated to 37° C. with an ambient relative humidity level of 35% (absolute humidity equal to 102 lbs. of moisture per lb. of dry air), and with the $CO_2$ detection system referenced under these conditions. The $CO_2$ gas level is maintained at 5% of the environment. Water is now placed in the incubator to raise its humidity level to saturation. After stabilization, the temperature remains at 37° C. and the relative humidity in the incubator should now be 98% (absolute humidity equal to 308 grains of moisture per lb. of dry air). The $CO_2$ concentration is based on the displayed value which is zero corrected (humidity compensated) for the relative humidity change from the original incubator setup humidity level. A verification of the actual $CO_2$ concentration reveals that the level has remained at 5% of the incubator's environment.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A humidity compensated carbon dioxide gas detection and control system in a substantially saturated or non-saturated gaseous environment which comprises:
   a humidity sensor means capable of providing a humidity level output;
   a thermal conductivity sensor means capable of providing a carbon dioxide concentration output;
   means for comparing said humidity level output with a stored humidity level output to establish a compensation value, said stored humidity level is the stored humidity level output at the initial zero reference of said carbon dioxide gas;
   means for adjusting said carbon dioxide concentration output in accordance with said compensation value, thereby generating a humidity compensated carbon dioxide gas concentration output; and
   means for controlling the flow of carbon dioxide gas into said environment in accordance with said humidity compensated carbon dioxide gas concentration output.

2. The system according to claim 1 wherein said means for controlling the flow of carbon dioxide gas is a microprocessor and a solenoid valve.

3. The system according to claim 1 further comprising a means for measuring the temperature of said environment.

4. The system according to claim 3 further comprising a means for adjusting said humidity level output in accordance with said temperature.

5. The system according to claim 1 wherein said humidity sensor means is a monolithic integrated circuit.

6. The system according to claim 5 wherein said monolithic integrated circuit is coupled with a thin film platinum RTD sensor which is capable of measuring the temperature of said environment.

7. The system according to claim 5 wherein said monolithic integrated circuit is a complimentary metal oxide semiconductor having a capacitance sensor.

8. The system according to claim 1 wherein said thermal conductivity sensor means is a differential thermometer.

9. The system according to claim 8 wherein said differential thermometer comprises an electronic bridge circuit and a pair of thermistors.

10. The system according to claim 1 wherein said means for comparing said humidity level output with said stored humidity level output is a microprocessor.

11. The system according to claim 10 wherein said microprocessor includes a look-up table which comprises differential data that represents specific values to offset the $CO_2$ gas control system zero reference point.

12. The system according to claim 1 wherein said means for adjusting said carbon dioxide concentration output in accordance with said compensation value is a microprocessor.

13. A process for measuring and controlling carbon dioxide gas in a substantially saturated or non-saturated environment which comprises:
   measuring the humidity level of said environment;
   measuring the carbon dioxide concentration of said environment;
   comparing said humidity level with a stored humidity level to establish a compensation value, said stored humidity level is the stored humidity level output at the initial zero reference of said carbon dioxide gas;
   adjusting said carbon dioxide concentration in accordance with said compensation value, thereby generating a humidity compensated carbon dioxide gas concentration measurement; and
   controlling the flow of said carbon dioxide gas into said environment in accordance with said humidity compensated carbon dioxide gas concentration measurement.

14. The process according to claim 13 wherein the flow of carbon dioxide gas into said environment is controlled by a microprocessor and a solenoid valve.

15. The process according to claim 13 further comprising the step of measuring the temperature of said environment.

16. The process according to claim 15 further comprising a means for adjusting said humidity level output in accordance with said temperature.

17. The process according to claim 13 wherein said humidity level is measured by a monolithic integrated circuit.

18. The process according to claim 17 wherein said monolithic integrated circuit is coupled with a thin film platinum RTD sensor which is capable of measuring the temperature of said environment.

19. The process according to claim 17 wherein said monolithic integrated circuit is a complimentary metal oxide semiconductor having a capacitance sensor.

20. The process according to claim 13 wherein said carbon dioxide gas concentration is measured by a differential thermometer.

21. The process according to claim 20 wherein said differential thermometer comprises an electronic bridge circuit and a pair of thermistors.

22. The process according to claim 13 wherein the humidity level of said environment is compared with said stored humidity via microprocessor.

23. The process according to claim 22 wherein said microprocessor includes a look-up table which comprises differential data that represents specific values to offset the $CO_2$ gas control system zero reference point.

24. The process according to claim 13 wherein said carbon dioxide concentration is adjusted with said compensation value via a microprocessor.

* * * * *